United States Patent
Kawashima et al.

(10) Patent No.: US 7,632,683 B2
(45) Date of Patent: Dec. 15, 2009

(54) METHOD, APPARATUS, REAGENT KIT AND REAGENT FOR DISTINGUISHING ERYTHROCYTES IN A BIOLOGICAL SPECIMEN

(75) Inventors: Yasuyuki Kawashima, Kobe (JP); Yasuhiro Sakai, Kobe (JP)

(73) Assignee: Sysmex Corporation, Kobe-shi (JP)

( * ) Notice: Subject to any disclaimer, the term of this patent is extended or adjusted under 35 U.S.C. 154(b) by 417 days.

(21) Appl. No.: 11/241,408

(22) Filed: Sep. 30, 2005

(65) Prior Publication Data

US 2006/0073601 A1    Apr. 6, 2006

(30) Foreign Application Priority Data

Sep. 30, 2004   (JP) .............................. 2004-289097

(51) Int. Cl.
*G01N 33/48*    (2006.01)
*G01N 21/75*    (2006.01)
*G01N 21/76*    (2006.01)

(52) U.S. Cl. .............................. 436/63; 436/10; 436/17; 436/164; 436/172; 422/73; 422/82.05; 422/82.08; 422/82.09; 435/4; 435/29

(58) Field of Classification Search ...................... 436/8, 436/10, 17, 63, 164, 165, 172, 174; 422/73, 422/82.05, 82.08, 82.09; 435/4, 29
See application file for complete search history.

(56) References Cited

U.S. PATENT DOCUMENTS

| 4,622,298 A | * | 11/1986 | Mansour et al. ................ 435/34 |
| 5,325,169 A |   | 6/1994  | Nakamoto et al. |
| 5,693,484 A | * | 12/1997 | Nakamoto et al. ............. 435/39 |
| 5,731,867 A | * | 3/1998  | Katayama ..................... 356/73 |
| 5,891,733 A | * | 4/1999  | Inoue ........................... 436/63 |
| 2002/0076743 A1 | * | 6/2002 | Sakai et al. .................... 435/34 |

FOREIGN PATENT DOCUMENTS

| EP | 1136563 A2 | 9/2001 |
| EP | 1413889 A2 | 4/2004 |
| JP | H09-329596 A | 12/1997 |

OTHER PUBLICATIONS

Breslin, W.J.; Phillips, J.E.; Lomax, L.G.; Bartels, M.J.; Dittenber, D.A.; Calhoun, L.L; and Miller, R.R. "Hemolytic Activity of Ethylene Glycol Phenyl Ether (EGPE) in Rabbits"; *Fundamental and Applied Toxicology*, 1991, 17, 466-481.

(Continued)

*Primary Examiner*—Maureen M Wallenhorst
(74) *Attorney, Agent, or Firm*—Brinks Hofer Gilson & Lione

(57) ABSTRACT

A method for distinguishing erythrocytes in a biological specimen, includes preparing a sample liquid so as to cause damage to a cell membrane of yeast-like fungi without hemolyzing erythrocytes in a biological specimen and to stain the yeast-like fungi with a fluorescent dye; detecting a first information and a second information from a particle in the sample liquid, wherein the first information reflects a size of the particle and the second information reflects a degree of fluorescent staining of the particle; and distinguishing the erythrocytes from the yeast-like fungi based on the first information and second information detected. An apparatus, a reagent kit and a reagent for carrying out the method are also disclosed.

13 Claims, 8 Drawing Sheets

OTHER PUBLICATIONS

King, M.A. "Detection of Dead Cells and Measurement of Cell Killing By Flow Cytometry"; *Journal of Immunological Methods*, 2000, 243, 155-166.

Russell, A.D. "Similarities and Differences in the Responses of Microorganisms to Biocides"; *Journal of Antimicrobial Chemotherapy*, 2003, 52, 760-763.

\* cited by examiner

US 7,632,683 B2

METHOD, APPARATUS, REAGENT KIT AND REAGENT FOR DISTINGUISHING ERYTHROCYTES IN A BIOLOGICAL SPECIMEN

This application claims priority under 35 U.S.C. §119 to Japanese Patent Application No. 2004-289097 filed Sep. 30, 2004, the entire content of which is hereby incorporated by reference.

FIELD OF INVENTION

The present invention relates to a method, an apparatus, a reagent kit and a reagent for distinguishing erythrocytes in a biological specimen such as urine, cerebrospinal fluid, or synovial fluid, and more particularly to a method, an apparatus, a reagent kit and a reagent for distinguishing erythrocytes in a biological specimen with improved precision for distinguishing erythrocytes appearing in the specimen from specific bacteria such as yeast-like fungi.

BACKGROUND

It is important in distinguishing nephropathies and uropathies to analyze the particles appearing in urine such as erythrocytes, leukocytes, epithelial cells, urinary casts, and bacteria. For example, erythrocytes are important in determining the presence or absence of bleeding in a path from the glomerulus of a kidney to the urethra. Also, increase in the number of leukocytes suggests inflammations or infections. In addition, by examining the morphology of erythrocytes or urinary casts, the derivation site thereof can be inferred.

Conventionally, as a technique for analyzing particles appearing in urine, a method has been used in which a stained urine specimen is mounted on a slide glass or a calculation board for observation with a microscope and the number of particles within the field of view are counted for each type of the particles. However, such a technique is a manual method, and imposes a burden on a person that uses the method. Moreover, variation tends to occur in the result of counting depending on the degree of the skill that the person who uses the method has.

In recent years, a technique has been developed in which the particles contained in urine are automatically classified and counted with the use of the flow cytometry method. With this method, a sample liquid prepared by performing fluorescence staining on a urine specimen is made to flow through a flow cell, and a laser beam is radiated into the flow cell. Then, the intensities of the forward scattered light and the fluorescence emitted from a particle in the sample liquid irradiated with the laser beam are measured. The intensity of the forward scattered light reflects the size of the particle. The larger the particle is, the larger the intensity of the forward scattered light will be. On the other hand, the intensity of the fluorescence reflects the degree of fluorescence staining of the particle. The intensities of the forward scattered light and the fluorescence differ depending on the kind of the particles. Therefore, by making analyses while combining such optical information, the kind of the particles can be determined, and the number of the particles can be counted. Such a technique is disclosed, for example, in the specification of U.S. Pat. No. 5,325,169.

However, by the method of the above-described U.S. Pat. No. 5,325,169, with a urine sample containing yeast-like fungi which are comparatively large bacteria, the intensities of the forward scattered light and the fluorescence detected from those particles will be of the same degree as those detected from erythrocytes, thereby sometimes making it difficult to distinguish the yeast-like fungi from the erythrocytes.

To such a problem, there is for example a method in which a result of measuring a sample liquid, which is prepared by adding a cell membrane damaging agent for hemolyzing the erythrocytes to a specimen containing erythrocytes and yeast-like fungi, with a flow cytometer, and a result of measuring a sample liquid prepared without adding the cell membrane damaging agent with a flow cytometer are obtained and compared so as to distinguish the erythrocytes from the yeast-like fungi and to count the number of the erythrocytes. Such a technique is disclosed, for example, in Japanese Patent Application Laid-Open (JP-A) Patent Publication No. H09-329596.

However, by the method disclosed in Japanese Patent Application Laid-Open (JP-A) Patent Publication No. H09-329596, a sample with hemolyzed erythrocytes and a sample without hemolyzing the erythrocytes are respectively measured, thereby increasing the amount of the specimen and the reagents needed for the measurement, and also increasing the time needed for the measurement.

BRIEF SUMMARY

In view of the above-mentioned problems, the present invention provides a method, an apparatus, a reagent kit and a reagent for distinguishing erythrocytes in a specimen more efficiently. Also, the present invention provides a method, an apparatus, a reagent kit and a reagent for distinguishing erythrocytes in a specimen with better precision.

A method for distinguishing erythrocytes in a biological specimen according to a first aspect of the present invention comprises the steps of: preparing a sample liquid by performing to give a damage to a cell membrane of yeast-like fungi without hemolyzing erythrocytes in a biological specimen and to stain the yeast-like fungi with a fluorescent dye; detecting a first information and a second information from a particle in the sample liquid, wherein the first information reflects a size of the particle and the second information reflects a degree of fluorescent staining of the particle; and distinguishing the erythrocytes from the yeast-like fungi based on the first information and second information detected.

A method for distinguishing erythrocytes in a biological specimen according to a second aspect of the present invention comprises the steps of: preparing a sample liquid by performing to give a damage to a cell membrane of yeast-like fungi without hemolyzing erythrocytes in a urine specimen and to stain the yeast-like fungi with a fluorescent dye; detecting intensity of scattered light and intensity of fluorescence from a particle in the sample liquid; and distinguishing the erythrocytes from the yeast-like fungi based on the intensity of scattered light and intensity of fluorescence detected.

An apparatus for distinguishing erythrocytes in a biological specimen according to a third aspect of the present invention comprises: a sample preparing section having a specimen container for containing a biological specimen, a first reagent container for containing a first reagent including a substance that gives a damage to a cell membrane of yeast-like fungi without hemolyzing erythrocytes in a biological specimen, a second reagent container for containing a second reagent including a fluorescent dye to stain the yeast-like fungi, a mixing section for preparing a sample liquid by mixing the first and second reagents with the biological specimen, and a supplying mechanism for supplying the biological specimen contained in the specimen container, the to said mixing section first reagent contained in the first reagent container and the second reagent contained in the second reagent container to the mixing section; a detecting section for detecting a first information and a second information from a particle in the sample liquid, wherein the first information reflects a size of the particle and the second information reflects a degree of fluorescent staining of the particle; and a controlling section for distinguishing the erythrocytes from the yeast-like fungi based on the first and second information detected.

A reagent kit for distinguishing erythrocytes in a biological specimen analyzing particles in a specimen according to a fourth aspect of the present invention comprises: a first reagent containing a substance that gives a damage to a cell membrane of yeast-like fungi without hemolyzing erythrocytes in a biological specimen; and a second reagent containing a fluorescent dye to stain the yeast-like fungi.

A reagent for distinguishing erythrocytes in a biological specimen analyzing particles in a specimen according to a fifth aspect of the present invention comprises: a substance that gives a damage to a cell membrane of yeast-like fungi without hemolyzing erythrocytes in a biological specimen; and a fluorescent dye to stain the yeast-like fungi.

According to the present invention, even with a specimen containing yeast-like fungi, the erythrocytes can be distinguished more efficiently than in the prior art by improving the fluorescence stainability of the yeast-like fungi without hemolyzing the erythrocytes. Also, according to the present invention, the erythrocytes can be distinguished with better precision.

DETAILED DESCRIPTION OF THE PREFERRED EMBODIMENTS

Figure 1:
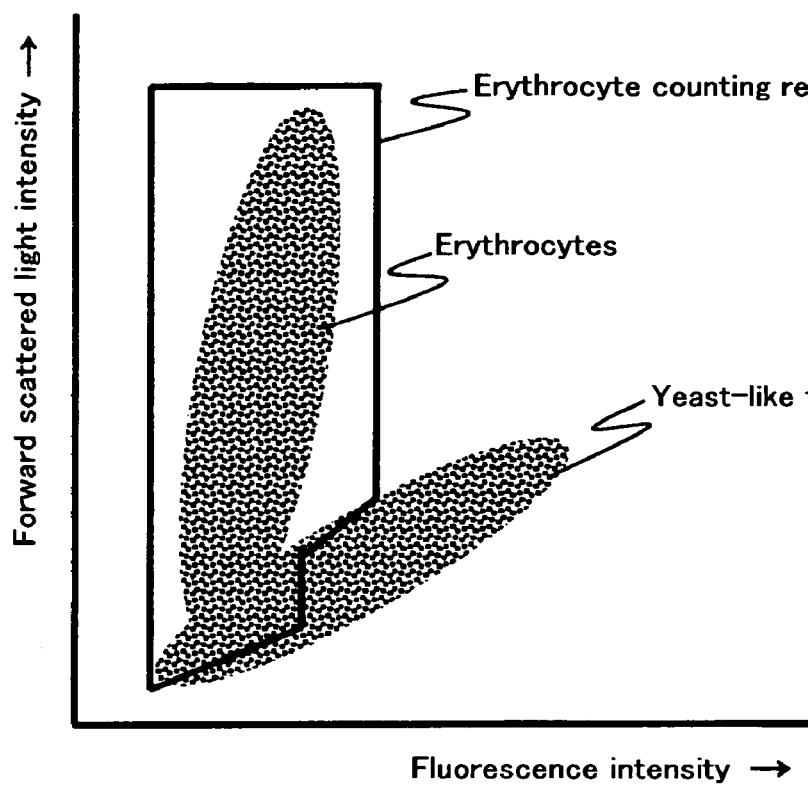
FIG. 1 is a model view describing a two-dimensional scattergram obtained by a conventional method.

Hereafter, an embodiment of the present invention will be described. However, the present invention is not limited to this embodiment. In this embodiment, a sample liquid is prepared by mixing a urine specimen with a predetermined reagent to perform fluorescence staining of the particles in the urine. Then, from each particle contained in the sample liquid, information reflecting the size of the particle and information reflecting the degree of staining of the particle are detected. By analyzing those information, the erythrocytes are distinguished from other particles and the number thereof is counted.

As a method for detecting information reflecting the size of the particle and information reflecting the degree of staining of the particle, the flow cytometry method can be used, for example. A flow cytometer is an apparatus for automatically performing the method. A flow cytometer includes a flow cell for making the sample liquid flow therethrough, a laser light source for radiating a laser beam to the sample liquid flowing through the flow cell, a photoelectric conversion element for receiving a scattered light and a fluorescence emitted from the particles in the sample liquid irradiated with the laser beam and converting into electric signals in accordance with the intensities of the lights, and a signal processing circuit for extracting the signal intensities of the electric signals for each particle that is output by the photoelectric conversion element. The intensity of the scattered light emitted from a particle constitutes information reflecting the size of the particle. The intensity of the fluorescence emitted from a particle constitutes information reflecting the degree of fluorescence staining of the particle. As the scattered light, those scattered in the extending direction of the optical axis of the laser beam that is incident into the particle or in the surrounding direction thereof (forward scattered light), those scattered in the direction perpendicular to the optical axis of the laser beam that is incident into the particle or in the surrounding direction thereof (side scattered light), or those scattered in other directions can be raised as examples. These can be used as information reflecting the size of the particle. Particularly, however, a forward scattered light is suitably used.

Here, for detection of information reflecting the size of the particle, a detector of electric resistance type may be used as well. With the detector of electric resistance type, particles are let to pass through a narrow through-hole to which a voltage is applied, and the change in electric resistance during the passage is captured as an electric signal. Since the signal intensity thereof differs depending on the size (volume) of the particle, this can be used as information reflecting the size of the particle.

By defining the range of the fluorescence intensity and the scattered light intensity that the erythrocytes have (or the intensity of the electric signal for each particle detected by the detector of electric resistance type) in advance, whether the particle is an erythrocyte or not can be determined by determining whether the signal detected from each particle falls within the range or not.

As the reagent for preparing a sample liquid by mixing with a specimen, a staining liquid containing a fluorescent dye for staining the particles in the urine specimen and a diluting liquid containing a substance that adjusts the environment for performing a fluorescence staining process on the specimen can be used. By mixing the specimen with the diluting liquid and the staining liquid, a sample liquid for analysis is prepared.

As described above, when yeast-like fungi are present in a urine specimen, the intensities of the forward scattered light and the fluorescence detected from the yeast-like fungi may overlap with the intensities detected from the erythrocytes, making it difficult to distinguish the erythrocytes from the yeast-like fungi. Therefore, by allowing the diluting liquid to contain a substance that gives a difference to the staining property of the fluorescence dye between the yeast-like fungi and the erythrocytes, the precision of distinguishing the erythrocytes can be improved, because there will be difference in the fluorescence intensities detected from the yeast-like fungi and the erythrocytes. Such a substance may be, for example, a substance that promotes the dye penetration into the inside of the cell by giving a damage to the cell membrane of the yeast-like fungi. When there is no damage in the cell membrane of the yeast-like fungi, the fluorescent dye is bonded only to the cell membrane surface. In contrast, when there is a damage in the cell membrane, the fluorescent dye goes not only to the cell membrane surface but also into the inside of the cell to be bonded to the intracellular substance such as the nucleic acids, thereby improving the fluorescence stainability. Here, as the substance that promotes the dye penetration into the inside of the cell by giving a damage to the cell membrane of the yeast-like fungi, those not excessively giving damage to the cell membrane of the erythrocytes are used. When the cell membrane of the erythrocytes is excessively damaged, hemolysis occurs, making it difficult to count the number of the erythrocytes. The substance satisfying the above conditions may be, for example, a nonionic organic compound having a benzene ring. For example, aromatic alcohols such as benzyl alcohol, β-phenethyl alcohol, phenol, 1-phenoxy-2-propanol, and 2-phenoxyethanol, phenyl acetate, and benzothiazole compounds such as 2-aminobenzothiazole and benzothiazole can be used. Among these, 2-phenoxyethanol is particularly suitably used.

Here, in order to improve the solubility of each of the aforementioned substances, the diluting liquid may contain a surfactant such as MTAB, DTAB, or OTAB. Here, when the concentration of the above surfactant is high, there is a fear of hemolyzing the erythrocytes, so that the surfactant is preferably used at a concentration that does not hemolyze the erythrocytes.

The diluting liquid preferably contains a buffer agent and an osmotic pressure compensating agent so as to keep the buffer capacity within the ranges of the osmotic pressure and the pH value that do not hemolyze the erythrocytes. The pH value of the diluting liquid is typically within a range of 7.0 to 9.0, preferably 7.1 to 8.6, more preferably 7.1 to 7.8, still more preferably 7.3 to 7.8. This is due to the following reason. When the pH value of the diluting liquid exceeds 9.0 to make the diluting liquid strongly alkaline, there is a fear of hemolyzing the erythrocytes. In an acidic region, the pH change in the urine specimen is large, so that there is a fear of giving a damage to the erythrocytes or decrease in the overall stainability of the particles in the urine.

As the buffer agent to be contained in the diluting liquid, conventionally known ones can be used. For example, Good buffer agents such as Tris and MES, Bis-Tris, ADA, PIPES, ACES, MOPSO, BES, MOPS, TES, HEPES, DIPSO, TAPSO, POPSO, HEPPSO, EPPS, Tricine, Bicine, and TAPS can be raised as examples. Among these, HEPES is preferable. The buffer agent is used at a concentration that keeps the pH value within a predetermined range when the urine specimen is diluted, in accordance with the buffer capacity of the buffer agent to be used. Typically, the concentration is 20 to 500 mM, preferably 50 to 200 mM.

As the osmotic pressure compensating agent to be contained in the diluting liquid, inorganic salts, organic salts such as propionates, sugars, and the like are used. As the inorganic salts, sodium chloride, potassium chloride, sodium bromide, and the like are used. As the propionates among the organic salts, sodium propionate, potassium propionate, ammonium propionate, and the like are used. As other organic salts, oxalates and acetates are used. As the sugars, sorbitol, glucose, mannitol, and the like are used. The osmotic pressure compensating agent is added for the purpose of preventing hemolysis of the erythrocytes and obtaining a stable fluorescence intensity. The osmotic pressure of the urine are distributed in a wide range from 50 to 1300 mOsm/kg. When the osmotic pressure of the analyzing reagent is too low, the hemolysis of the erythrocytes will proceed at an early stage, whereas when the osmotic pressure is too high, the damage of the particles in the urine will be large. Therefore, the osmotic pressure is preferably from 100 to 600 mOsm/kg, more preferably from 150 to 500 mOsm/kg.

Also, in order to reduce the effect of amorphous salts (for example, ammonium phosphate, magnesium phosphate, and calcium carbonate) appearing in the urine, for dissolving these, a chelate agent for dissolving these may be contained in the diluting liquid. The kind of the chelate agent is not particularly limited as long as it is a calcium-removing agent or a magnesium-removing agent. For example, an EDTA salt, CyDTA, DHEG, DPTA-OH, EDDA, EDDP, GEDTA, HDTA, HIDA, Methyl-EDTA, NTA, NTP, NTPO, EDDPO, and the like can be raised as examples. An EDTA salt, CyDTA, and GEDTA are suitably used. The chelate agent is used typically at a concentration within a range from 0.05 to 5 W/W %, preferably from 0.1 to 1 W/W %. Here, the calcium-removing agent and the magnesium-removing agent herein referred to mean those bonded to calcium ions or magnesium ions to form a water-soluble compound.

As the fluorescent dye for staining the particles contained in the urine, a condensed benzene derivative represented by the following chemical formula can be used, for example.

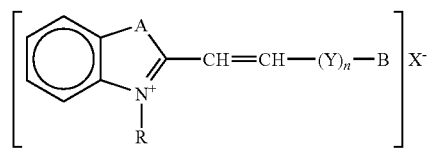

[In the formula, A represents —O—, —S—, or —C(CH$_3$)$_2$—; R represents a lower alkyl group; X represents a halogen; Y represents —CH= or —NH—; n represents 0 or 1; and B represents

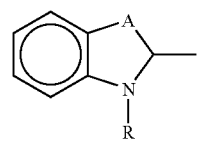

(In the formula, A and R have the same meaning as the above) or a phenyl group substituted with two lower alkoxy groups or with one di(lower alkyl)amino group (this lower alkyl group may be substituted with a cyano group).]. The above lower alkyl group means an alkyl group having one to six carbon atoms, and methyl, ethyl, propyl, butyl, isobutyl, pentyl, and hexyl can be raised as examples. As the halogen atom of X, fluorine, chlorine, bromine, and iodine can be raised as examples. Also, the phenyl group substituted with two lower alkoxy groups in B means a phenyl group substituted with two $C_{1-3}$ alkoxy groups, preferably C1-2 alkoxy groups, for example, methoxy groups and ethoxy groups. Specifically, 2, 6-dimethoxy phenyl group and 2, 6-diethoxyphenyl group can be raised as examples. Also, the phenyl group substituted with a di(lower alkyl)amino group (the lower alkyl group may be substituted with a cyano group) in B means a phenyl group substituted with a C1-3 alkylamino group, preferably a C1-2 alkylamino group. Here, the alkyl group may be substituted with a cyano group and includes, for example, methyl, ethyl, cyanomethyl, cyanoethyl, and the like. As a preferable phenyl group substituted with a di(lower alkyl)amino group (the lower alkyl group may be substituted with a cyano group), 4-dimethylaminophenyl group, 4-diethylaminophenyl group, 4-(cyanoethylmethylamino)phenyl group, and the like can be raised as examples. As a specific example of such a condensed benzene derivative, those represented by the following chemical formula can be raised.

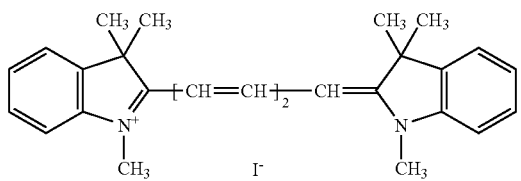

This dye is commercially available from Nippon Kanko Shikiso Kenkyuusho Co., Ltd.

The above dye is a polymethine fluorescent dye, and a fluorescence is excited by radiating a red laser beam having a wavelength of 633 nm. Here, in addition to the above, as a fluorescent dye to be contained in the staining liquid, a suitable one can be selected for use in accordance with the wavelength of the laser beam for exciting the fluorescence.

Since many fluorescent dyes are unstable in an aqueous solution, the preservation stability of a fluorescent dye can be enhanced by using those obtained by dissolving the fluorescent dye in a water-soluble organic solvent as a staining liquid. The water-soluble organic solvent is preferably a lower alkanol, a lower alkylene glycol, or a lower alkylene glycol mono(lower alkyl) ether. For example, methanol, ethanol, n-propanol, ethylene glycol, diethylene glycol, triethylene glycol, ethylene glycol monomethyl ether, ethylene glycol monoethyl ether, and the like can be used. Among these, ethylene glycol, diethylene glycol, and triethylene glycol are preferable, and ethylene glycol is more preferable in view of the influence on the particles in the urine, the viscosity, and the like. The fluorescent dye is typically used at 1 to 20 ppm, preferably 3 to 12 ppm, more preferably 3 to 9 ppm, as the final concentration of the sample liquid for analysis.

Here, instead of using the staining liquid and the diluting liquid as separate liquids, a one-liquid reagent obtained by allowing a fluorescent due to being contained in a diluting liquid may be used.

Figure 2:
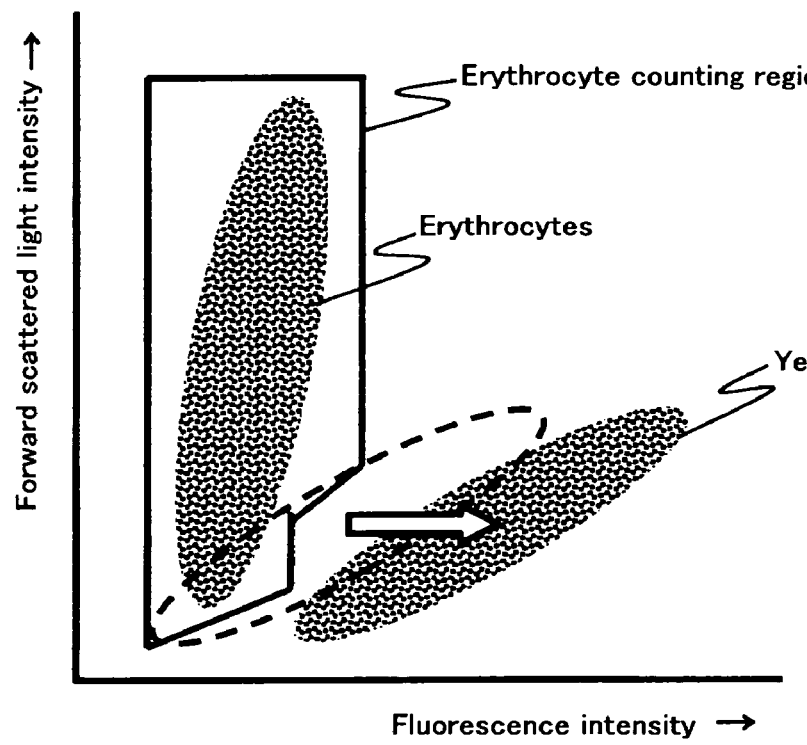
FIG. 2 is a model view describing a two-dimensional scattergram obtained in one embodiment of the present invention.

FIGS. 1 and 2 are model views showing a two-dimensional scattergram taking, as axes, the forward scattered light intensity and the fluorescence intensity for each particle obtained by the flow cytometer from a urine sample liquid containing erythrocytes and yeast-like fungi. In both of the two views, the vertical axis represents the forward scattered light intensity, and the horizontal axis represents the fluorescence intensity. In this coordinate space, the forward scattered light intensity increases according as the particle goes upward, and the fluorescence intensity increases according as the particle goes to the left. The erythrocyte counting region R is for counting the number of erythrocytes by assuming that the dots having a forward scattered light intensity and a fluorescence intensity within the corresponding range are erythrocytes. In each view, the colony of the dots corresponding to the erythrocytes appears in the erythrocyte counting region R. Also, the colony of the dots corresponding to the yeast-like fungi is shown in each view.

FIG. 1 shows a two-dimensional scattergram obtained by a urine sample liquid prepared by a conventional method. Some of the dots corresponding to the yeast-like fungi are within the erythrocyte counting region R. In such a case, the result of counting the number of erythrocytes will be greater than the actual one, so that it will be difficult to determine a correct number of erythrocytes.

On the other hand, FIG. 2 shows a two-dimensional scattergram obtained from a urine sample liquid prepared by the method of the present invention. The positions at which the dots corresponding to the yeast-like fungi appear move to the left as compared with FIG. 1 (the positions in FIG. 1 are shown with a broken line), and do not overlap with the erythrocyte counting region R. This is because the intensity of the fluorescence detected from the yeast-like fungi increase by action of the substance that improves the stainability of the yeast-like fungi. This substance does not give a damage to the cell membrane of the erythrocytes, so that there will be no inconvenience in detecting and counting the erythrocytes.

EXAMPLE 1

Hereafter, an Example of the present invention will be described. In this Example, erythrocytes in urine are detected with an apparatus for analyzing particles in urine, which uses urine of a human as a specimen and employs the flow cytometry method.

Specimen

In this Example, a specimen was used which was obtained by adding purely cultured yeast-like fungi (*C. glabrata*) at a concentration of about 100 fungi/µl to urine of a human being containing erythrocytes.

Reagent

A staining liquid and a diluting liquid having the following compositions were used as the reagent to be used in the apparatus for analyzing particles in urine.

Staining Liquid

A staining liquid was used which was obtained by dissolving a fluorescent dye represented by the following formula in ethylene glycol so that the final concentration in the sample for analysis would be 6 ppm.

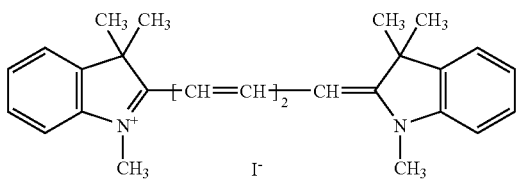

Diluting Liquid

A diluting liquid was used which was obtained by dissolving the following substances into purified water.

| HEPES | 11.9 g/l |
|---|---|
| Sodium propionate | 5.98 g/l |
| EDTA-3K | 4.0 g/l |
| 2-phenoxyethanol | 7.5 g/l |
| Sodium hydroxide | at an amount that gives a pH value of 7.0 |

Apparatus for Analyzing Particles in Urine

Figure 3:
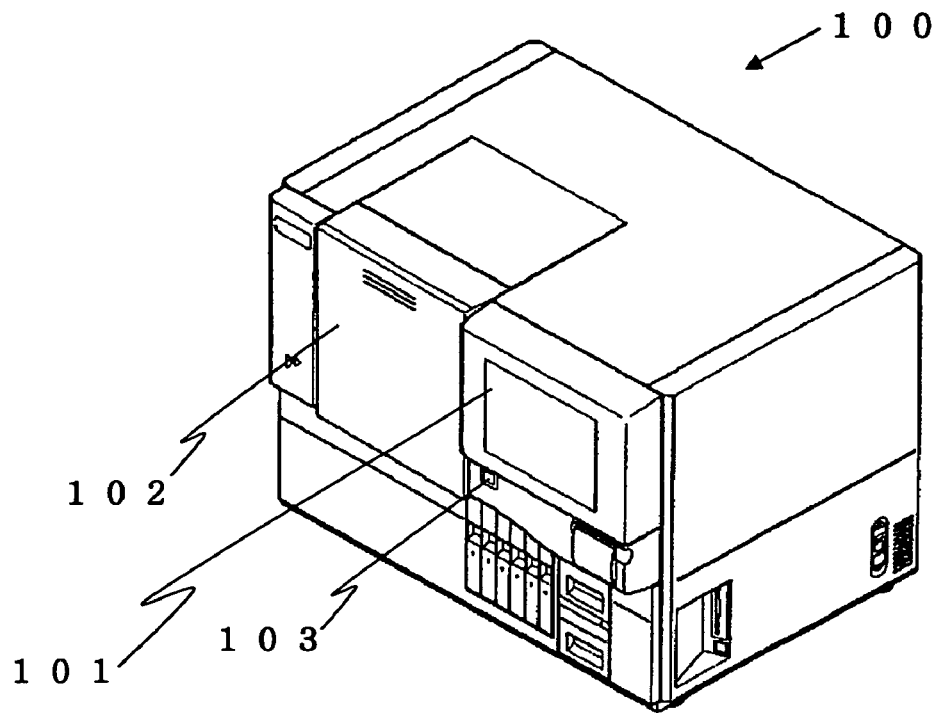
FIG. 3 is a view describing an outlook of an apparatus for analyzing particles in urine according to one embodiment of the present invention.
Figure 4:
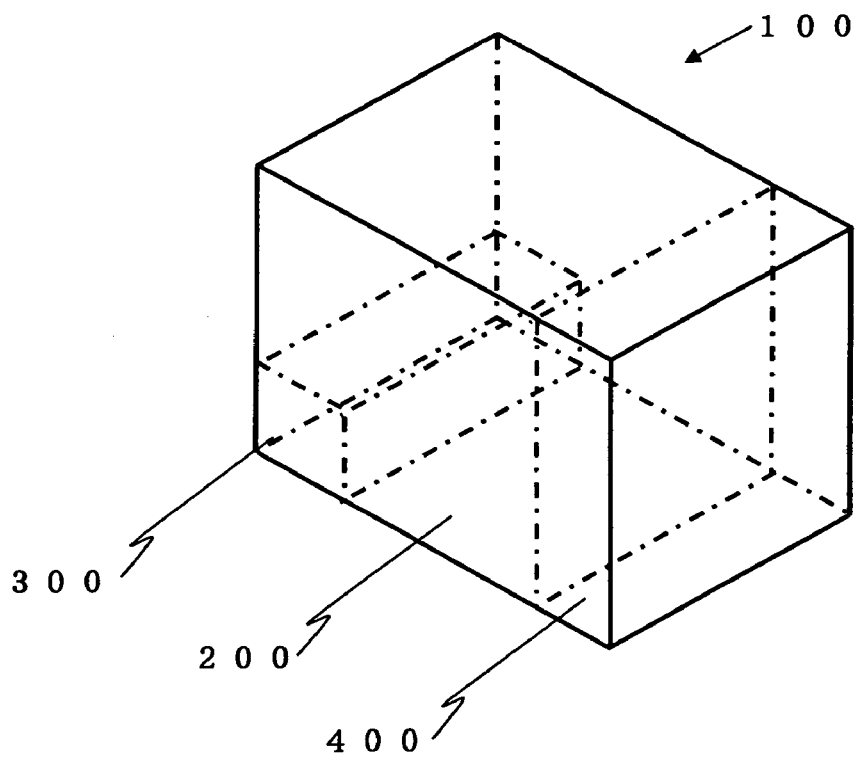
FIG. 4 is a view describing an inside configuration of the apparatus for analyzing particles in urine according to one embodiment of the present invention.

FIG. 3 shows an outlook of an apparatus for analyzing particles in urine 100 used in this Example. The front surface of the apparatus is provided with a liquid crystal touch panel 101 for performing various setting inputs and displaying and outputting the analysis results, a cover 102 that covers the later-mentioned sample preparing section 200, and a starting switch 103. FIG. 4 shows an inside configuration of the apparatus 100. A space located to the right of the apparatus is provided with a controlling section 400 that controls the operation of the apparatus and the analysis processes. A space located to the lower left of the apparatus is provided with a detecting section 300 for detecting signals from the sample liquid. Also, the rest of the space is provided with a sample preparing section 200 for preparing a sample liquid.

Hereafter, each of the sample preparing section 200, the detecting section 300, and the controlling section 400 will be described.

Configuration of Sample Preparing Section 200

Figure 5:
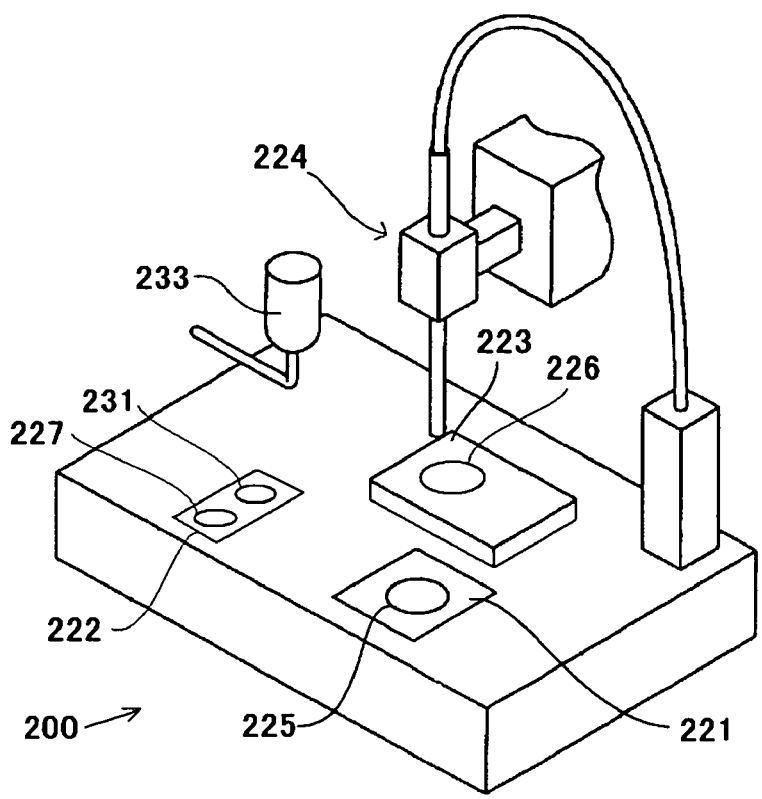
FIG. 5 is a view describing a sample preparing section of the apparatus for analyzing particles in urine according to one embodiment of the present invention.

FIG. 5 is a descriptive view showing the sample preparing section 200. The sample preparing section 200 includes a specimen setting section 221 located to the front right, a reagent setting section 222 located to the front left, and an incubator 223 located in the rear. Also, a dispensing device 224 is provided. When an operator opens the above-mentioned cover 102 of FIG. 3, the sample preparing section 200 shown in FIG. 5 appears. The sample preparing section 200 is constructed in such a manner that a specimen container 225 containing a specimen is set in the specimen setting section 221; a reaction vessel 226 is set in the incubator 223; and a reagent container 227 containing a staining liquid and a reagent container 231 containing a diluting liquid are set in the reagent setting section 222. The incubator 223 is adapted to vibrate and agitate the liquid in the set reaction vessel 226 while maintaining a predetermined temperature. The dispensing device 224 is adapted to suck and eject a predetermined amount of liquid through the tip end thereof, and is constructed to be capable of moving up and down, to the right and left, and to the front and rear by a driving device (not illustrated). The sample container 233 is connected to a flow cell 301 of the later-mentioned detecting section 300.

Configuration of Detecting Section 300

Figure 6:
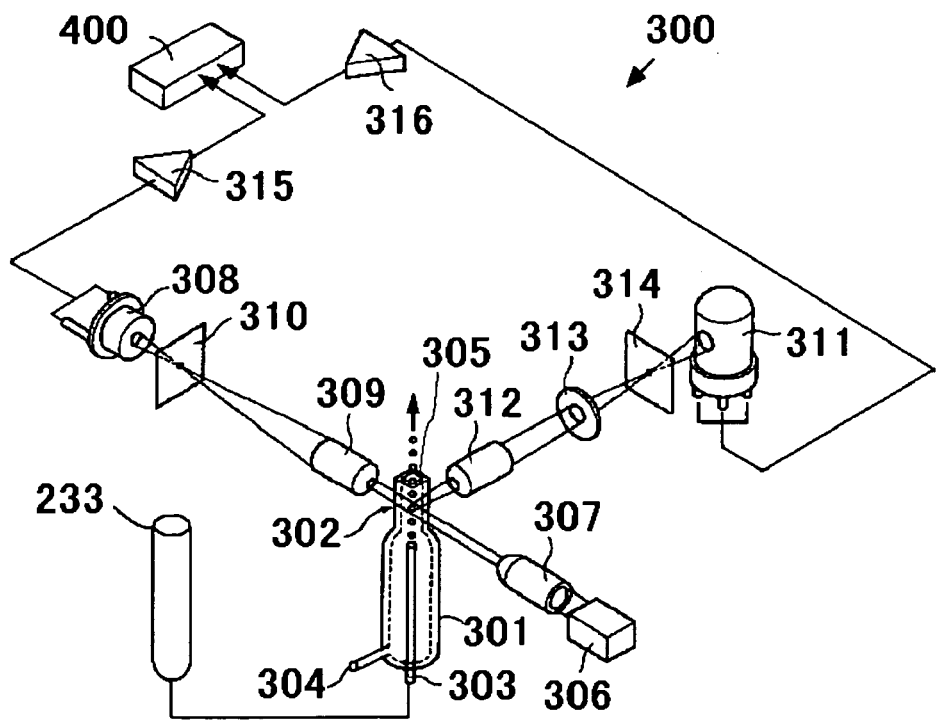
FIG. 6 is a view describing a detecting section of the apparatus for analyzing particles in urine according to one embodiment of the present invention.

FIG. 6 is a descriptive view showing a configuration of the detecting section 300. The detecting section 300 has a flow cell 301 for making the sample liquid flow. The flow cell 301 has an orifice section 302 which constitutes a portion to be irradiated with a laser beam and whose inside flow passageway is narrowed down, a nozzle 303 that jets the sample liquid upward toward the orifice section, a sheath liquid inlet 304, and an exhaust liquid outlet 305. The detecting section 300 has a laser light source 306 for radiating a laser beam. The laser light source 306 is a red semiconductor laser light source that emits a laser beam having a wavelength of 633 nm. The semiconductor laser light source is small as compared with a conventional gas laser light source represented by an argon ion laser light source, and has an advantage of having a long oscillation life. The detecting section 300 further has a condenser lens 307 that condenses the laser beam emitted from the laser light source 306 to the flow cell 301, a photodiode 308 that receives the forward scattered light emitted from the particle in the sample liquid irradiated with the laser beam and converts it into an electric signal, a collector lens 309 and a pinhole 310 for condensing the forward scattered light to the photodiode 308, a photomultiplier tube 311 that receives the fluorescence emitted from the particle in the sample liquid irradiated with the laser beam and converts it into an electric signal, a collector lens 312 for condensing the fluorescence to the photomultiplier tube 311, a filter 313, a pinhole 314, and amplifiers 315, 316 that amplify the electric signals output from the photodiode 308 and the photomultiplier tube 311 and outputs them to the controlling section 400 as a forward scattered light signal and a fluorescence signal.

Configuration of Controlling Section 400

Figure 7:
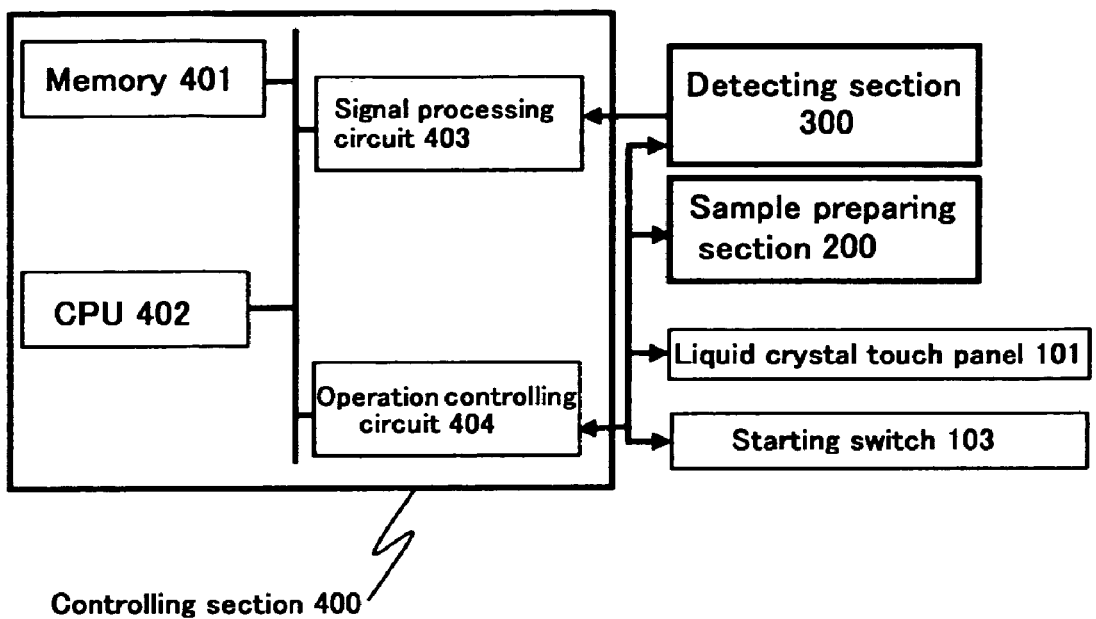
FIG. 7 is a view describing a controlling section of the apparatus for analyzing particles in urine according to one embodiment of the present invention.

FIG. 7 is a block diagram showing a configuration of the controlling section 400 and a relationship between the controlling section 400 and each section of the apparatus. The controlling section 400 includes a memory 401, a central calculation processing unit (CPU) 402, a signal processing circuit 403 that processes the signals sent from the detecting section 300, and an operation controlling circuit 404 for controlling the operation of each section of the apparatus 100. The memory 401 stores analyzing programs related to analysis of the signals obtained from particles such as erythrocytes and bacteria contained in a sample liquid, and controlling programs for controlling the operation of each section of the apparatus. The memory 401 also stores data processed by the signal processing circuit 403 and process results obtained by the analyzing programs. The CPU 402 executes the analyzing programs and controlling programs that are read out from the memory 401, processes and analyzes the signals detected from the sample liquid in the detecting section 300, or and sends the signals for controlling the operation of each section of the apparatus to the operation controlling circuit 404. The analysis results obtained by the analyzing programs are output to the liquid crystal touch panel 101.

Figure 8:
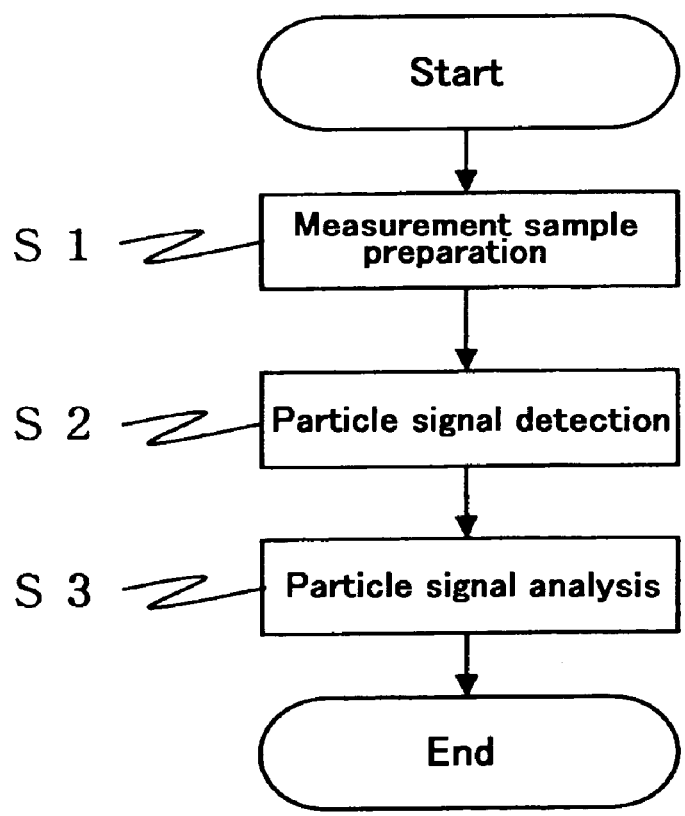
FIG. 8 is a flowchart describing an overall control of the apparatus for analyzing particles in urine according to one embodiment of the present invention.

Hereafter, the operation of the apparatus 100 will be described in detail. FIG. 8 is a flowchart showing an overall control of the apparatus 100 by the controlling programs. When an operator presses a starting switch 103, the controlling programs are started, and the step S1 (preparation of a sample liquid for analysis), the step S2 (detection of particle signals), and the step S3 (analysis of the particle signals) are successively executed. By this, each section of the sample preparing section 200, the detecting section 300, and the controlling section 400 is controlled, and a series of operations of the apparatus 100 are automatically executed. The operation of each section of the apparatus in the above steps S1, S2, and S3 will be described below.

Step S1 (Preparation of Sample Liquid for Analysis)

In the step S1, the sample preparing section 200 is controlled to execute the preparation of a sample for analysis. The operation of the sample preparing section 200 in the step S1 will be described with reference to FIG. 5. First, the dispensing device 224 sucks 522 µL of a diluting liquid from the sample container 231 of the reagent setting section 222, and then sucks 180 □L of a specimen (human urine) from the specimen container 225 that is set in the specimen setting section 221. The dispensing device 224 then dispenses the sucked diluting liquid and specimen to the reaction vessel 226 that is set in the incubator 223. Next, the dispensing device 224 sucks 18 µL of a staining liquid from the reagent container 227 of the reagent setting section 222, and dispenses the staining liquid to the reaction vessel 226. Thereafter, the incubator 223 stirs the mixture for 10 seconds to stain the diluted specimen while keeping the liquid temperature within the reaction vessel 226 containing the specimen, diluting liquid, and staining liquid to be 35□. The sample liquid for analysis thus prepared is sucked by the dispensing device 224, and is supplied to the sample container 233. The sample liquid for analysis supplied to the sample container 233 is let to flow through the flow cell 301 of the detecting section 300.

Step S2 (Detection of Particle Signals)

In the step S2, the detecting section 300 is controlled to detect signals reflecting the characteristics of each particle from the particles in the sample liquid for analysis. The operation of the detecting section 300 in the step S2 will be described with reference to FIG. 6. When the sample liquid is supplied to the sample container 233 as described above, the sample liquid is guided to the nozzle 303 by the operation of pumps and valves (not illustrated). Then, the sample liquid is ejected from the nozzle 303 to the flow cell 301. Simultaneously with this, a sheath liquid is supplied to the flow cell 301 from a sheath liquid container (not illustrated) via a sheath liquid inlet 304. By this, the sample liquid is surrounded by the sheath liquid in the flow cell 301, and is further narrowed down at by the orifice section 302 to flow. By narrowing the flow of the sample liquid, the particles such as erythrocytes and bacteria contained in the sample liquid are arranged in one line to flow through the orifice section 302. A laser beam emitted from the laser light source 306 is condensed by the condenser lens 307 and is radiated to the sample liquid that is flowing through the orifice section 302. The forward scattered light emitted from a particle in the sample liquid irradiated with the laser beam is condensed by the collector lens 309. Then the forward scattered light that has passed through the pinhole 310 is received and subjected to photoelectric conversion by the photodiode 308 to become a pulse-like forward scattered light signal. The fluorescence emitted from the particle in the sample liquid irradiated with the laser beam is condensed by the collector lens 312. Then the fluorescence that has passed through the filter 313 and the pinhole 314 is received and subjected to photoelectric conversion by the photomultiplier tube 311 to become a pulse-like fluorescence signal. The forward scattered light signal and the fluorescence signal are amplified respectively by the amplifiers 315, 316 and are sent to the controlling section 400.

Step S3 (Analysis of the Particle Signals)

Figure 9:
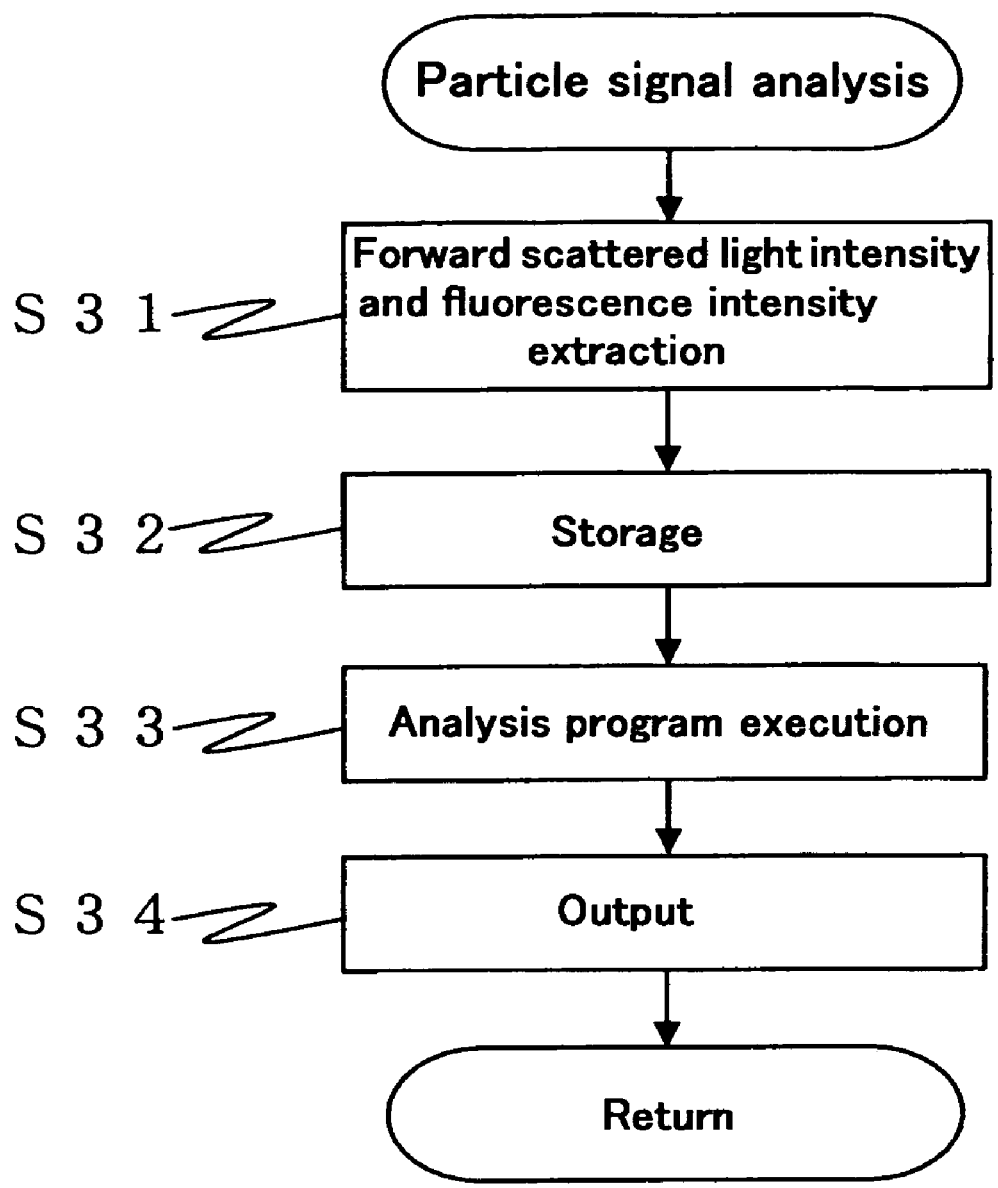
FIG. 9 is a flowchart describing an operation of particle signal analysis of the apparatus for analyzing particles in urine according to one embodiment of the present invention.

The forward scattered light signal and the fluorescence signal detected by the detecting section 300 in the step S3 are analyzed in the controlling section 400 in accordance with the flow shown in FIG. 9 (steps S31 to S34).

Step S31:

First, the forward scattered light signal and the fluorescence signal detected by the detecting section are input into the signal processing circuit 403. For each of the forward scattered light signal and the fluorescence signal, this signal processing circuit 403 regards a portion of a series of signal waveforms exceeding a predetermined signal intensity as a signal of detection of a particle. Then, the peak value of the signal intensity is extracted for each particle. The peak value of the forward scattered light signal is defined as a forward scattered light intensity, and the peak value of the fluorescence signal is defined as a fluorescence intensity.

Step S32:

The forward scattered light intensity and the fluorescence intensity obtained in the above step S31 are stored in the memory 401 as data for each particle.

Figure 10:
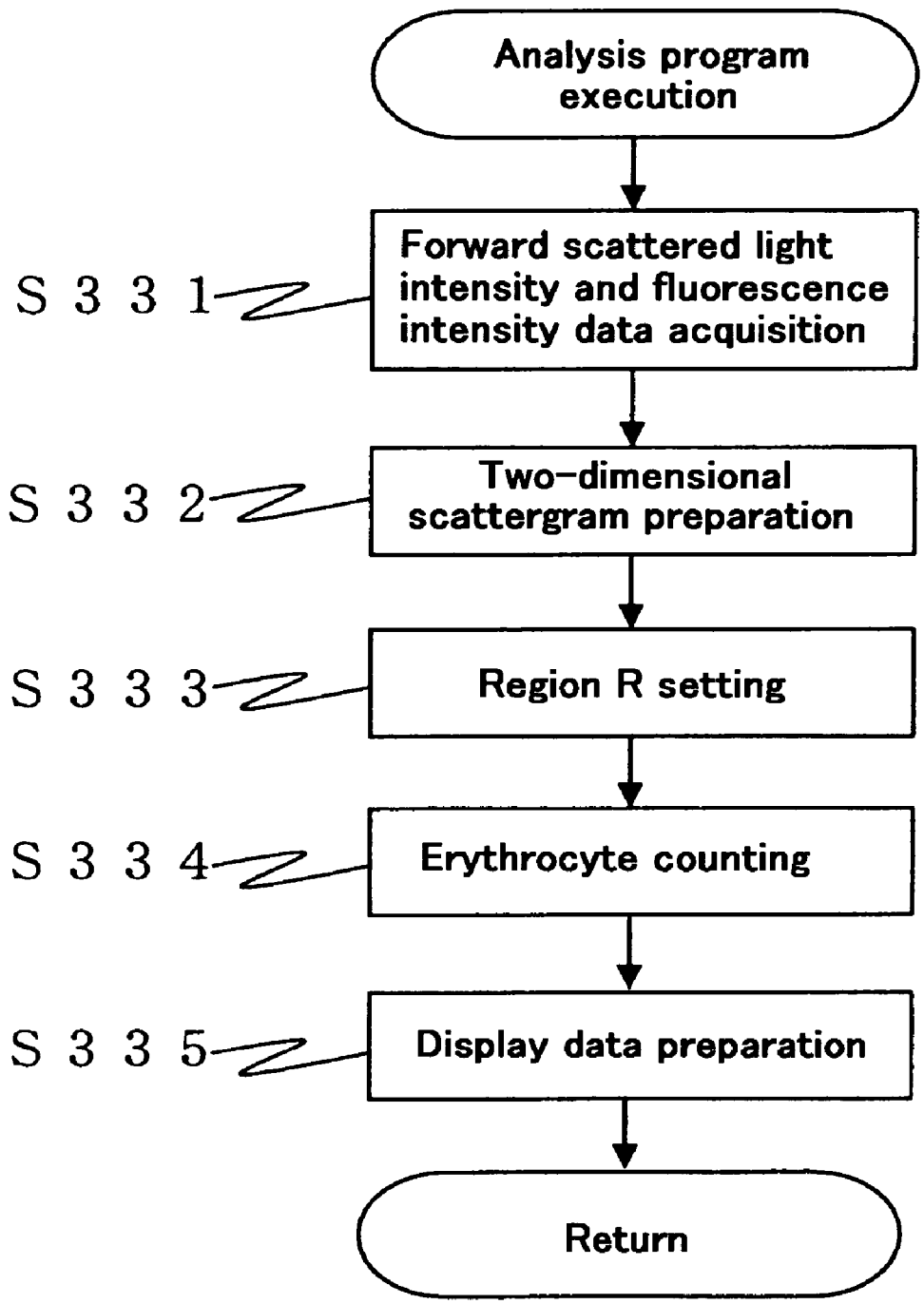
FIG. 10 is a flowchart describing each step of an analyzing program executed by the apparatus for analyzing particles in urine according to one embodiment of the present invention.

Step S33:

The data of the forward scattered light intensity and the fluorescence intensity stored in the memory 401 for each particle are analyzed by the analyzing programs stored in advance in the memory 401. Each step of the analyzing programs that are read out and executed by the CPU 402 will be described with reference to the flowchart of FIG. 10.

Step S331:

The data of the forward scattered light intensity and the fluorescence intensity corresponding to each particle in the sample for analysis are obtained from the memory 401.

Step S332:

The data of the forward scattered light intensity and the fluorescence intensity are developed into a two-dimensional coordinate space, so as to prepare a two-dimensional scattergram using the forward scattered light intensity and the fluorescence intensity as parameters.

Step S333:

An erythrocyte counting region R is set on the two-dimensional scattergram prepared in the step S332. The erythrocyte counting region R is a region that is set so as to regard the particles having a forward scattered light intensity and a fluorescence intensity within the region as erythrocytes for counting the number of the erythrocytes. The coordinate data of the erythrocyte counting region R, which are stored in advance in the memory 401, are read out by the analyzing programs in this step, and are applied to the two-dimensional scattergram. Here, the position of the erythrocyte counting region R is determined on the basis of the forward scattered light intensities and the fluorescence intensities obtained from the particles in urine that have been confirmed in advance to be erythrocytes by microscopic test or the like.

Figure 11:
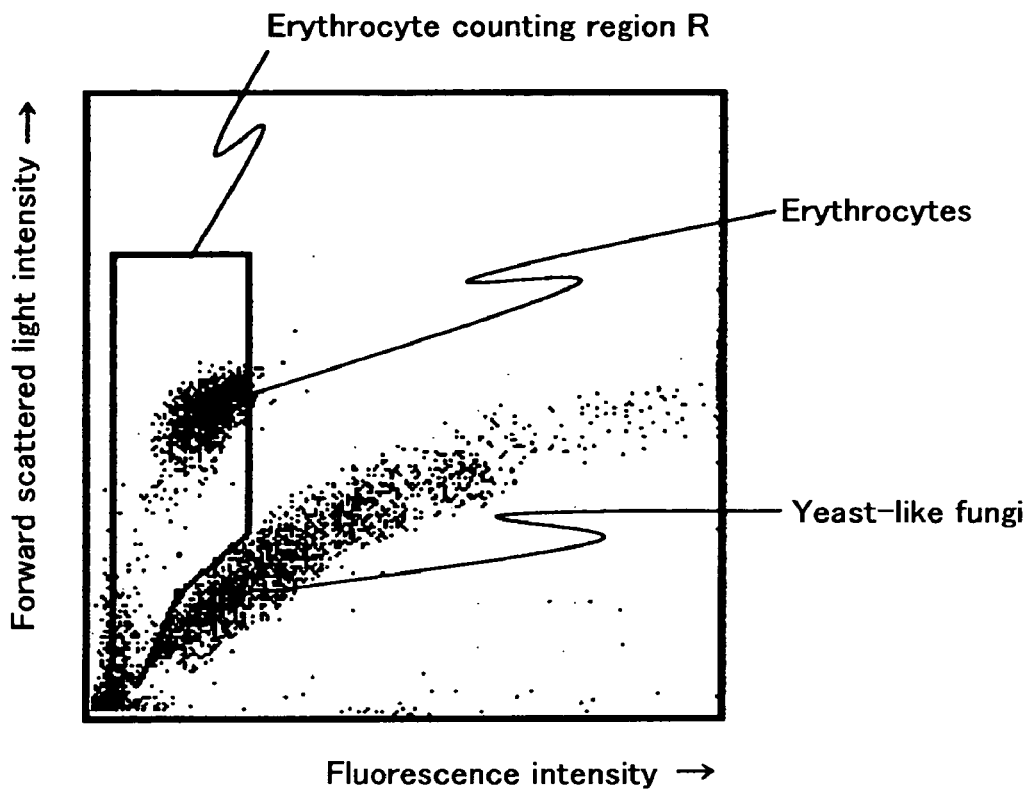
FIG. 11 is a view showing one example of a two-dimensional scattergram prepared by the apparatus for analyzing particles in urine according to one embodiment of the present invention.

FIG. 11 shows one example of a two-dimensional scattergram prepared in the above step S333. In the two-dimensional scattergram, the vertical axis represents the forward scattered light intensity, and the horizontal axis represents the fluorescence intensity. In this coordinate space, the forward scattered light intensity increases according as the particle goes upward, and the fluorescence intensity increases according as the particle goes to the left. An erythrocyte counting region R is set. Also, the dots corresponding to the particles in the sample liquid appear on the two-dimensional scattergram.

Step S334:

The number of dots appearing in the erythrocyte counting region R is counted. Then, the number of erythrocytes contained in a unit amount of the specimen is calculated on the basis of this number of dots, the ratio of diluting the specimen in the preparation of the sample for analysis, and the volume of the sample liquid that has been let to flow through the flow cell.

Step S335:

Data are prepared for outputting the two-dimensional scattergram prepared as shown above and the results of counting the erythrocytes to the liquid crystal touch panel 101 as analysis results, and the prepared data are stored in the memory 401. The above is a step that is executed by the analyzing programs in the step S33. Subsequently, the procedure goes to the step S34 of the flow shown in FIG. 9.

Figure 12:
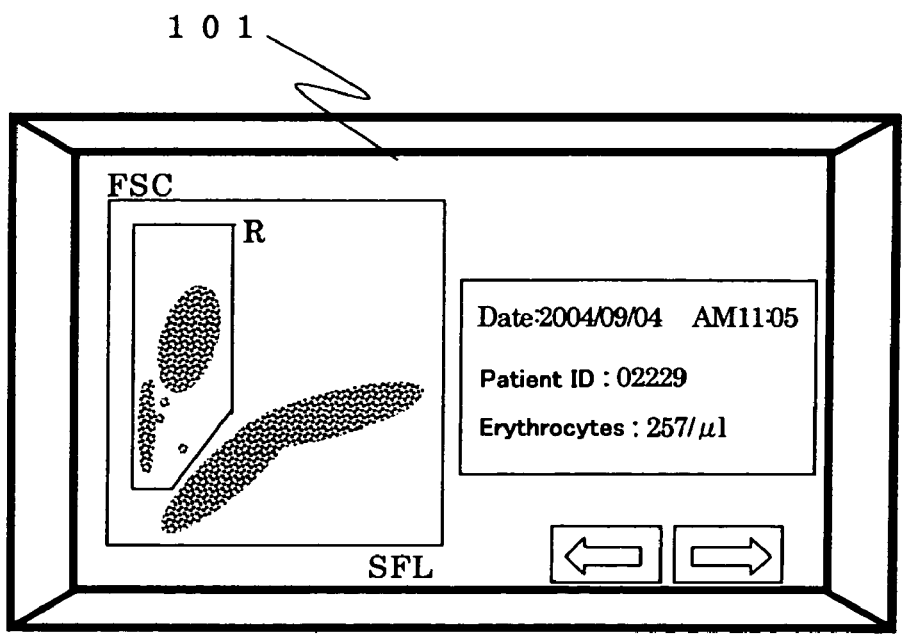
FIG. 12 is a view showing how a result of analysis is displayed on a liquid crystal touch panel of the apparatus for analyzing particles in urine according to one embodiment of the present invention.

Step S34:

The data of the analysis results stored in the memory 401 in the above step S335 are output to the liquid crystal touch panel 101. FIG. 12 is a model view showing how the above data are output to the liquid crystal touch panel 101. The liquid crystal touch panel 101 displays the two-dimensional scattergram and the number of erythrocytes as the analysis results.

Example of Analysis Results

FIG. 11 is a two-dimensional scattergram obtained by analyzing the above specimen with the apparatus 100. The vertical axis represents the forward scattered light intensity, and the horizontal axis represents the fluorescence intensity. In this coordinate space, the forward scattered light intensity increases according as the particle goes upward, and the fluorescence intensity increases according as the particle goes to the left. The erythrocyte counting region R is a region that is set so as to regard the particles having a forward scattered light intensity and a fluorescence intensity within the region as erythrocytes for counting the number of the erythrocytes. The colony of dots corresponding to the erythrocytes appears in the region. On the other hand, it will be understood that the colony of dots corresponding to the yeast-like fungi does not enter the erythrocyte counting region R.

EXAMPLE 2

In contrast to the Example 1, a urine specimen was analyzed using a diluting liquid having the following composition in the apparatus 100. This diluting liquid is different from the one used in the Example 1 in that the diluting liquid does not contain 2-phenoxyethanol. The specimen, the staining liquid, and the apparatus for analyzing particles in urine that were put to use are same with those used in the Example 1.

Diluting Liquid

A diluting liquid was used which was obtained by dissolving the following substances into purified water.

| | |
|---|---|
| HEPES | 11.9 g/l |
| Sodium propionate | 5.98 g/l |
| EDTA-3K | 4.0 g/l |
| Sodium hydroxide | at an amount that gives a pH value of 7.0 |

Figure 13:
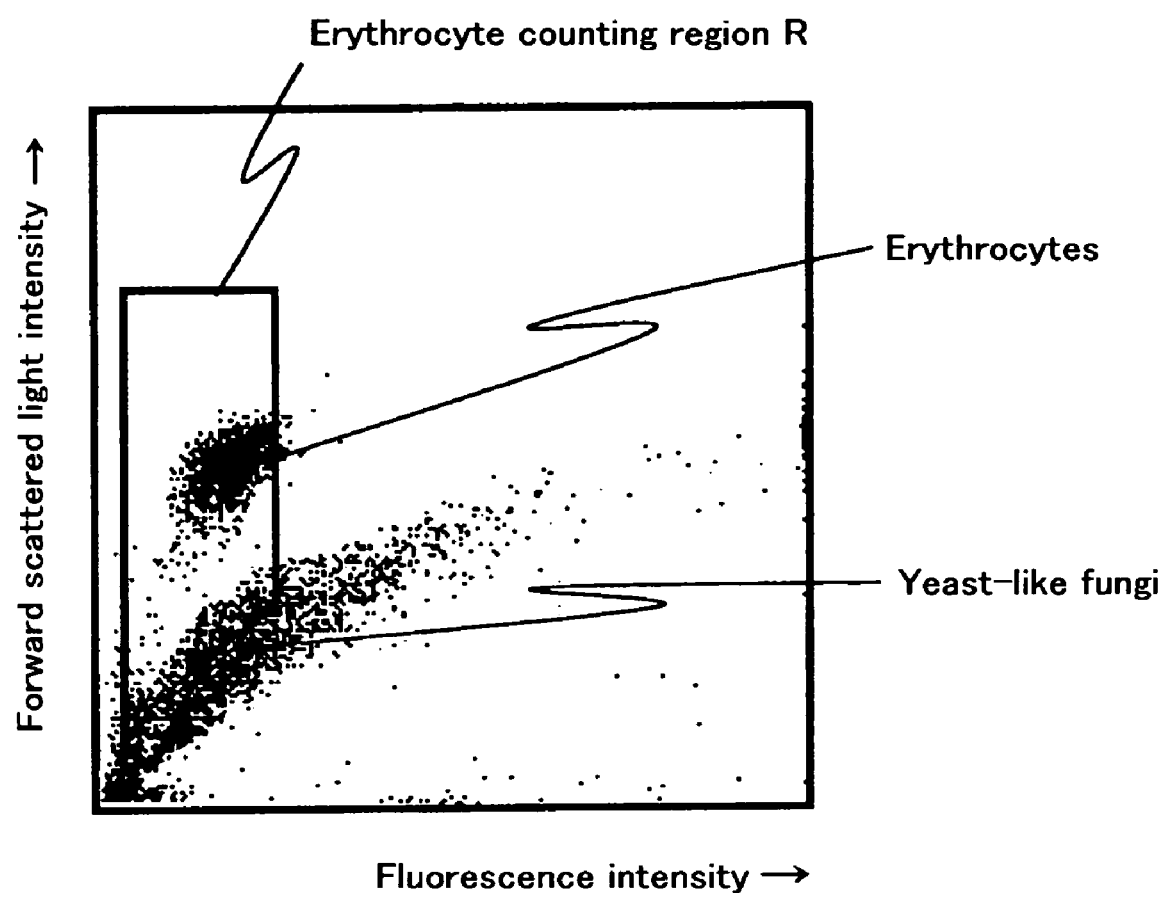
FIG. 13 is a view showing one example of a two-dimensional scattergram prepared by the apparatus for analyzing particles in urine according to one embodiment of the present invention.

FIG. 13 shows a two-dimensional scattergram obtained in this Example. In this view, it will be understood that part of the colony of dots corresponding to the yeast-like fungi enters the erythrocyte counting region R. Comparing this Example 2 with the aforesaid Example 1, it will be surmised that 2-phenoxyethanol acted on the yeast-like fungi in the specimen to promote the penetrating property of the dye in the above Example 1, so that the yeast-like fungi came to have a larger fluorescence intensity than the erythrocytes.

EXAMPLE 3

Four kinds of diluting liquids having different pH values were prepared by changing the content of sodium hydroxide in the diluting liquid used in the Example 1. They were diluting liquids 1 to 5 having different pH values in five stages including the diluting liquid used in the Example 1 (diluting liquid 1: pH 7.0, diluting liquid 2: pH 7.1, diluting liquid 3: pH 7.3, diluting liquid 4: pH 7.8, diluting liquid 5: pH 8.6). With the use of these diluting liquids, a urine specimen was analyzed. A specimen was used which was obtained by adding purely cultured yeast-like fungi (*C. glabrata*) at a concentration of about 100 fungi/(l to urine of a human being that does not contain erythrocytes. The staining liquid and the apparatus for analyzing particles in urine that were put to use are same with those of the Example 1. Then, in the analysis using each diluting liquid, an average value of the fluorescence signal intensities obtained from the yeast-like fungi was calculated. The result thereof is shown in the following Table 1. Here, the values of the fluorescence intensity are relative values when the minimum value of the horizontal axis is set at 0 and the maximum value is set at 255 in the two-dimensional scattergram obtained by the apparatus for analyzing particles in urine 100 shown in FIGS. 11 and 13.

TABLE 1

| Diluting liquid put to use | Diluting liquid 1 | Diluting liquid 2 | Diluting liquid 3 | Diluting liquid 4 | Diluting liquid 5 |
|---|---|---|---|---|---|
| pH of diluting liquid | 7.0 | 7.1 | 7.3 | 7.8 | 8.6 |
| Average value of fluorescence intensity | 84 | 85 | 86 | 94 | 98 |

In Table 1, in a range from neutral to weakly alkaline such as when the pH value of the diluting liquid is from 7.0 to 8.6, the fluorescence stainability of the yeast-like fungi improves according as the alkalinity increases. This shows that, by selecting a pH value that improves the fluorescence stainability of the yeast-like fungi to make a larger difference from the fluorescence intensity of the erythrocytes, the distinction between the two will be more certain.

EXAMPLE 4

Diluting liquids were prepared using other substances instead of 2-phenoxyethanol that was contained in the diluting liquid used in the Example 1 as a substance that acts on the yeast-like fungi to promote the penetration property of the dye. A urine specimen was analyzed using these diluting liquids. The specimen, the staining liquid, and the apparatus for analyzing particles in urine apparatus that were put to use are same with those of the Example 3. Then, in the analysis using each diluting liquid, an average value of the fluorescence signal intensities obtained from the yeast-like fungi was calculated. The names of the substances contained in the diluting liquids in place of 2-phenoxyethanol and the average values of the fluorescence signal intensities obtained from the yeast-like fungi are shown in the following Table 2. Here, the concentration of each substance in the diluting liquids is 1.0 wt % in all cases. In the same manner as in the Example 3, the values of the fluorescence intensity are relative values when the minimum value of the horizontal axis is 0 and the maximum value is 255 in the two-dimensional scattergram obtained by the apparatus 100 shown in FIGS. 11 and 13.

TABLE 2

| Substance name | Fluorescence intensity |
| --- | --- |
| β-phenethyl alcohol | 84 |
| Benzyl alcohol | 73 |
| Phenol | 55 |
| 1-phenoxy-2-propanol | 103 |
| Phenyl acetate | 82 |
| 2-aminobenzothiazole | 70 |
| Benzothiazole | 92 |

Here, according to an experiment of the present inventors, when a diluting liquid not containing a substance that improves the fluorescence stainability of the yeast-like fungi such as substances shown in Table 2 was used, the average value of the fluorescence signal intensities obtained from the yeast-like fungi was about 20 to 50. Therefore, it will be understood that, by allowing each substance shown in Table 2 to be contained in the diluting liquid, the fluorescence stainability of the yeast-like fungi will be greatly improved. By selecting and using a suitable one from the above substances in a combination of the fluorescent dye used for fluorescence staining and each substance in the reagent, there will be greater difference in the fluorescence intensity between the yeast-like fungi and the erythrocytes, so that the distinction between the two will be more certain.

In each of the above Examples, improvement of the precision for distinguishing erythrocytes by improving ement of the fluorescence stainability of the yeast-like fungi has been mentioned. However, this technique can also be applied to a case in which chained *Staphylococcus* is present in a specimen to inhibit the distinction of the erythrocytes. Each of the cells of *Staphylococcus* is small as compared with an erythrocyte, so that it does not usually affect the distinction of erythrocytes. However, when *Staphylococcus* is chained, the apparent size thereof may become large and overlap with the size of the erythrocyte, thereby making an accurate distinction difficult. In such a case, the erythrocytes can be distinguished with good precision by improving the fluorescence stainability of *Staphylococcus* using the reagent described above.

Also, in the above Examples, urine is used as a specimen; however, the present invention is not limited to this alone. The specimen may be, for example, cerebrospinal fluid, synovial fluid, lymph fluid, pleural effusion, ascites fluid, sputum, mucus such as pharyngeal mucus or nasal mycteric mucus, washings such as trachea washings, secretion such as urethral secretion or vaginal secretion, exudate such as vulnus exudate or purulent puric exudate, or the like.

It will be obvious to those having skilled in the art that many changes may be made in the above-described details of the preferred embodiments of the present invention. The scope of the present invention, therefore, should be determined by the following claims.

The invention claimed is:

1. A method for distinguishing erythrocytes in a biological specimen, comprising:
preparing a sample liquid by mixing a reagent comprising a nonionic organic compound selected from the group consisting of an aromatic alcohol and a benzothiazole compound with a biological specimen for causing damage to a cell membrane of yeast-like fungi without hemolyzing erythrocytes in the biological specimen and staining the yeast-like fungi with a fluorescent dye;
detecting first information and second information from particles in the sample liquid, wherein the first information reflects a size of the particle and the second information reflects a degree of fluorescent staining of the particle; and
distinguishing the erythrocytes from the yeast-like fungi based on the first information and second information detected.

2. The method of claim 1, wherein the nonionic organic compound is 2-phenoxyethanol.

3. The method of claim 1, wherein the fluorescence staining is carried out in an environment having a pH value of 7.0 to 9.0.

4. The method of claim 1, wherein the first information is intensity of scattered light that is emitted from a particle irradiated with light.

5. The method of claim 1, wherein the second information is intensity of fluorescence that is emitted from a particle irradiated with light.

6. The method of claim 1, wherein the specimen is urine.

7. The method of claim 1, wherein the nonionic organic compound is selected from the group consisting of benzyl alcohol, β-phenethyl alcohol, phenol, 1-phenoxy-2-propanol, 2-phenoxyethanol, phenyl acetate, 2-aminobenzothiazole, and benzothiazole.

8. A method for distinguishing erythrocytes in a urine specimen, comprising:
preparing a sample liquid by mixing a reagent comprising a nonionic organic compound selected from the group consisting of an aromatic alcohol and a benzothiazole compound with a urine specimen for causing damage to a cell membrane of yeast-like fungi without hemolyzing erythrocytes in the urine specimen and staining the yeast-like fungi with a fluorescent dye;
detecting intensity of scattered light and intensity of fluorescence from particles in the sample liquid; and
distinguishing the erythrocytes from the yeast-like fungi based on the intensity of scattered light and intensity of fluorescence detected.

9. The method of claim 8, wherein the nonionic organic compound is selected from the group consisting of benzyl alcohol, β-phenethyl alcohol, phenol, 1-phenoxy-2-propanol, 2-phenoxyethanol, phenyl acetate, 2-aminobenzothiazole, and benzothiazole.

10. An apparatus for distinguishing erythrocytes in a biological specimen comprising:
a sample preparing section comprising:
a specimen container for containing a biological specimen;
a first reagent container for containing a first reagent comprising a nonionic organic compound selected from the group consisting of an aromatic alcohol and a benzothiazole compound for causing damage to a cell membrane of yeast-like fungi without hemolyzing erythrocytes in a biological specimen;
a second reagent container for containing a second reagent comprising a fluorescent dye to stain the yeast-like fungi;
a mixing section for preparing a sample liquid by mixing the first and second reagents with the biological specimen; and
a supplying mechanism for supplying the biological specimen contained in the specimen container, the first reagent contained in the first reagent container and the second reagent contained in the second reagent container to the mixing section;
a detecting section for detecting first information and second information from particles in the sample liquid, wherein the first information reflects a size of the particle and the second information reflects a degree of fluorescent staining of the particle; and a controlling section for distinguishing the erythrocytes from the yeast-like fungi based on the first and second information detected.

11. The apparatus of claim 10, wherein the detecting section comprises:

a flow cell for making the sample liquid flow;

a light source for radiating a light to the sample liquid flowing in the flow cell;

a scattered light receiving section for detecting a scattered light emitted from a particle in the sample liquid irradiated with the light as the first information; and a fluorescence receiving section for detecting a fluorescence emitted from the particle in the sample liquid irradiated with the light as the second information.

12. The apparatus of claim 11, wherein the scattered light is forward scattered light.

13. The apparatus of claim 11, wherein the biological specimen is urine.

* * * * *

UNITED STATES PATENT AND TRADEMARK OFFICE
CERTIFICATE OF CORRECTION

PATENT NO.       : 7,632,683 B2                                    Page 1 of 1
APPLICATION NO.  : 11/241408
DATED            : December 15, 2009
INVENTOR(S)      : Kawashima et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 858 days.

Signed and Sealed this

Second Day of November, 2010

David J. Kappos
*Director of the United States Patent and Trademark Office*